United States Patent [19]

Robinson et al.

[11] 4,427,578

[45] Jan. 24, 1984

[54] AMORPHOUS SILICA-BASED CATALYST AND PROCESS FOR ITS PRODUCTION

[75] Inventors: Joseph G. Robinson, Winchcombe; David I. Barnes, Cheltenham; Angela M. Carswell, Longhope, all of England

[73] Assignee: Coal Industry (Patents) Limited, London, England

[21] Appl. No.: 396,132

[22] Filed: Jul. 7, 1982

[30] Foreign Application Priority Data

Aug. 18, 1981 [GB] United Kingdom ............... 8125108

[51] Int. Cl.³ .................................................. B01J 21/08
[52] U.S. Cl. ........................................ 502/177; 502/240; 502/258; 502/259; 502/256; 502/260
[58] Field of Search ................................ 252/459, 451

[56] References Cited

U.S. PATENT DOCUMENTS

| | | | |
|---|---|---|---|
| 3,313,739 | 4/1967 | Acker | 252/451 |
| 3,873,469 | 3/1975 | Foster et al. | 252/460 |
| 3,873,469 | 3/1975 | Foster et al. | 252/477 R |
| 4,080,284 | 3/1978 | Mitchell | 252/451 |
| 4,169,926 | 10/1979 | McDaniel | 252/451 |
| 4,190,457 | 2/1980 | McDaniel | 252/451 |

*Primary Examiner*—Delbert E. Gantz
*Assistant Examiner*—Lance Johnson
*Attorney, Agent, or Firm*—Stevens, Davis, Miller & Mosher

[57] ABSTRACT

This invention relates to a catalyst for use in the direct conversion of synthesis gas to olefinic hydrocarbons in good yield. It also relates to a process for producing the catalyst.

The catalyst comprises a highly porous amorphous silica support on which is deposited one or more monolayers of silica. The catalyst is then impregnated with a transition metal. The monolayer of silica is formed by the hydrolysis of a compound such as ethyl orthosilicate while it is adsorbed onto the support.

8 Claims, No Drawings

AMORPHOUS SILICA-BASED CATALYST AND PROCESS FOR ITS PRODUCTION

This invention relates to an amorphous silica based catalyst and to a process for its production. The catalyst will find particular but not exclusive use in the conversion of synthesis gas to olefinic hydrocarbons.

As the world's reserves of oil are being exhausted, much attention is being focussed on the use of coal as a feedstock for the preparation of substitutes for oil-based products. Processes are known whereby coal can be treated with steam and oxygen at elevated temperatures to produce synthesis gas, comprising predominantly carbon monoxide and hydrogen. Synthesis gas offers a useful starting material for the production of substitutes for oil-based products.

In known processes synthesis gas is first catalytically converted into methanol. The methanol thus produced is then catalytically converted to olefinic hydrocarbons. The catalysts used in the conversion are generally based on aluminosilicates or zeolites which contain acid sites and which therefore cause the formation of unwanted by-products, particularly branched chain alkanes and aromatic hydrocarbons. Catalysts based on extremely low aluminium content aluminosilicates are also known, and are described, for instance, in U.S. Pat. No. 4,061,724. However, none of these catalysts enable the direct conversion of synthesis gas to olefinic hydrocarbons in high yield.

It is therefore an aim of the present invention to produce a catalyst which can be used in the direct conversion of synthesis gas to olefinic hydrocarbons in high yield.

Therefore, according to the present invention, there is provided a catalyst for synthesis gas conversion comprising a highly porous amorphous silica support, wherein the support has a monolayer of silica deposited on it and is impregnated with a transition metal, the catalyst having a maximum pore diameter of up to 5 nm. and an average pore diameter of up to 1.5 nm.

Highly porous amorphous silicas are known and are generally available as xerogels. A typical xerogel will have an average pore diameter of 2 nm, a maximum pore diameter of up to 5 nm., a surface area of 600–1000 m²/g and a pore volume of about 0.4 cc/g. The xerogel may be supplied in a range of particle sizes. Usually, substantially all its surface area is constituted by the pore walls. Xerogels do not exhibit any significant catalytic activity in the conversion of synthesis gas to other products, either untreated or when provided with a silica monolayer.

To produce a catalyst according to the invention from a silica support it is necessary to deposit a monolayer of silica on the surface of the support, and impregnate the whole catalyst with a transition metal.

Therefore according to a second aspect of the present invention there is provided a method of producing a catalyst for synthesis gas conversion comprising treating a support of a highly porous amorphous silica with a solution of a hydrolysable compound of silicon, removing the solvent to leave a monolayer of the compound on the surface area of the support, hydrolysing the compound to produce a monolayer of silica on the support and to produce a catalyst having a maximum pore diameter of up to 5 nm. and an average pore diameter of up to 1.5 nm., and impregnating the catalyst with a transition metal.

Preferably, the transition metal is iron, although other metals such as cobalt, chromium or nickel may also be used. The transition metal may be impregnated as a salt which is reduced to the metal. Conveniently the metal nitrate is used. Preferably the transition metal is carbided before the catalyst is used.

The catalyst preferably has an average pore diameter of about 0.5 nm. If the support has a large pore diameter originally, it may be necessary to deposit a second monolayer thereon in order to produce a catalyst having the appropriate pore diameter. The hydrolysable silicon compound used to deposit the silica layer on the support may be for instance ethyl orthosilicate or silicon (IV) chloride. The compound must be dissolved in an inert solvent. A lower alkane, for instance hexane, is particularly suitable. The hydrolysis may be carried out using water. However, if ethyl orthosilicate is used and water is used for hydrolysis, the reaction proceeds slowly, and it is therefore preferable to use a stronger hydrolysing agent, such as an ammoniacal alkanol solution. The Applicants have found that an ammoniacal solution of industrial methylated spirit is a suitable hydrolysing agent for ethyl orthosilicate.

It is envisaged that the catalyst will be of use in any of the conventional types of catalytic reactors, such as moving, fixed or fluidised bed reactors.

The invention will now be described by way of example only. The example describes a typical catalyst according to the invention, but should not be taken as an indication of the scope of the invention.

A catalyst was prepared using as a support a highly porous amorphous silica xerogel having the following properties:

| Pore Volume | 0.4 cc/g |
| --- | --- |
| Pore diameter | 2–3 nm |
| Surface Area | 800 m²/g |
| Particle size | 125 microns |

The xerogel support (100 g), in the form of beads, was heated at 150° C. for two hours in a dry atmosphere to remove any moisture physically adsorbed on the beads. The beads were held under reduced pressure and a cooled solution of ethyl orthosilicate in dry hexane was added over a period of about 20 minutes. The reduced pressure ensured that air trapped in the pores was released and replaced by solution. The mixture was allowed to stand at room temperature for about 16 hours. During this period it is believed that the ethyl orthosilicate at least in part reacted with hydroxyl groups on the surface of the support. The solvent is then evaporated off, leaving the partly or completely reacted ethyl orthosilicate attached to the surface of the support. The beads are then added to an excess of ammoniacal industrial methylated spirit with shaking. The pressure was slightly reduced to ensure complete pore penetration. The mixture was allowed to stand at room temperature for 16 hours, during which time the ethyl orthosilicate was completely hydrolysed, leaving a monolayer of silica on the support. The beads were washed free of the ethanol formed during the hydrolysis and were dried by heating to 150° C.

The support with its monolayer of silica was treated with an aqueous solution of ferrous nitrate. The solution was added to the beads until they were visibly moist. The beads were dried at 100° C. for about 1 hour and then at 110° C. for 12 hours. The ferrous nitrate was reduced to iron by passing a stream of hydrogen at 20 bar over the beads heated to 450° C. for 24 hours. The metallic iron thus formed was then carbided by passing synthesis gas at 7 bar over the beads heated to 250° C. for 48 hours. The catalyst thus produced had an average pore diameter of about 1.5 nm and was used to convert synthesis gas to olefinic hydrocarbons.

A fixed bed of the catalyst was used to treat synthesis gas having a molar ratio of hydrogen to carbon monoxide of about 1:1. The gas at 20 bar was passed over the catalyst at 300° C. at a low LHSV. The product gas had the following analysis.

| | |
|---|---|
| Methane | 15% |
| Ethylene | 4.2% |
| Ethane | 14.0% |
| Propene | 16.6% |
| Butanes | 5.2% |
| Residue | 45% |

The residue comprised hydrocarbons from $C_5$ to about $C_{12}$ and oxygenates formed from the carbon monoxide and hydrogen in the synthesis gas. It is thought that the cut-off in the product range at $C_{12}$ is due at least in part to the limitation on the pore diameter of the catalyst.

Thus the present invention provides a novel catalyst which can be used in the direct conversion of synthesis gas to olefinic hydrocarbons in good yield.

We claim:

1. A synthesis gas conversion catalyst comprising a highly porous amorphous silica xerogel support, a monolayer of silica deposited on the support, and a transition metal impregnated onto the silica-coated support, the catalyst having a maximum pore diameter of up to 5 nm and an average pore diameter of up to 1.5 nm.

2. A catalyst according to claim 1, and including a second monolayer of silica deposited on the first monolayer prior to impregnation with the transition metal.

3. A catalyst according to claim 2, wherein the average pore diameter is about 0.5 nm.

4. A catalyst according to claim 1, wherein the transition metal is iron.

5. A catalyst according to claim 1, wherein the transition metal is carbided.

6. A method of producing a synthesis gas conversion catalyst, comprising:
   1. treating a highly porous amorphous silica xerogel support with a solution of a hydrolysable compound of silicon in a solvent;
   2. removing the solvent to leave a monolayer of the compound on the surface area of the support;
   3. hydrolysing the compound to produce a monolayer of silica on the support; and
   4. impregnating the silica-coated support with a transition metal; thereby producing a catalyst having a maximum pore diameter of up to 5 nm and an average pore diameter of up to 1.5 nm.

7. A method according to claim 6, wherein step (3) is carried out using water or an ammoniacal solution of an alkanol.

8. A method according to claim 6, and including after step (3) a further step of depositing a second monolayer on the support, thereby to produce a catalyst having an average pore diameter of up to 0.5 nm.

* * * * *